United States Patent [19]

Odagiri et al.

[11] Patent Number: 4,739,075
[45] Date of Patent: Apr. 19, 1988

[54] REACTIVE END-CAPPING AGENT, ADDITION-CURABLE QUINOXALINE RESIN OLIGOMER AND INTERMEDIATE MATERIAL FOR FIBER-REINFORCED COMPOSITE

[75] Inventors: Nobuyuki Odagiri; Kuniaki Tobukuro, both of Otsu, Japan

[73] Assignee: Director-General of Agency of Industrial Science & Technology, Tokyo, Japan

[21] Appl. No.: 14,925

[22] Filed: Feb. 13, 1987

Related U.S. Application Data

[62] Division of Ser. No. 841,862, Mar. 20, 1986, Pat. No. 4,670,536.

[30] Foreign Application Priority Data

Jun. 1, 1985 [JP] Japan .................. 60-117708
Jun. 1, 1985 [JP] Japan .................. 60-117709

[51] Int. Cl.⁴ ............... C07D 491/052; C07D 209/56; C07D 209/76
[52] U.S. Cl. ...................... 548/431; 548/435
[58] Field of Search ................ 548/431, 435

[56] References Cited

U.S. PATENT DOCUMENTS

| | | | |
|---|---|---|---|
| 3,654,226 | 4/1972 | Augl et al. | 548/431 |
| 4,132,716 | 1/1979 | Kvita et al. | 548/431 |
| 4,139,533 | 2/1979 | Buchanan et al. | 548/435 |
| 4,552,931 | 11/1985 | St. Clair et al. | 525/432 |

Primary Examiner—Lucille M. Phynes
Attorney, Agent, or Firm—Austin R. Miller

[57] ABSTRACT

Disclosed in an alicyclic end-capping agent for a heterocyclic compound, which is represented by the formula [I]:

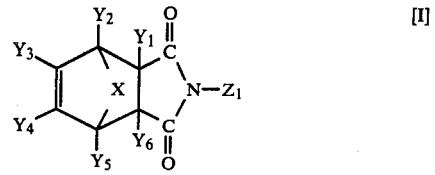

wherein X is CO, O, S, $CH_2$ or substituted $CH_2$, $Y_1$–$Y_6$ are halo, H, $NO_2$, aryl, alkaryl, arylalkyl or alkyl ether, and Z is

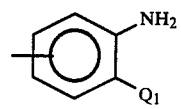

($Q_1$ is —$NH_2$, —SH, —OH or

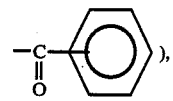

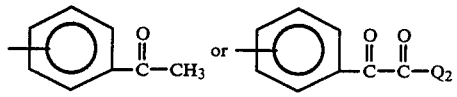

($Q_2$ is H, or monovalent aliphatic or amomatic group). Also disclosed is an addition-curable quinoxaline resin oligomer having the above-mentioned alicylic end-capping agents at both terminals of oligomer. This oligomer is useful especially for an intermediate material for a fiber-reinforced composite.

7 Claims, No Drawings

REACTIVE END-CAPPING AGENT, ADDITION-CURABLE QUINOXALINE RESIN OLIGOMER AND INTERMEDIATE MATERIAL FOR FIBER-REINFORCED COMPOSITE

This is a division of application Ser. No. 841,862 filed Mar. 20, 1986, now U.S. Pat. No. 4,670,536.

BACKGROUND OF THE INVENTION

1. Field of the Invention

The present invention relates to a novel end-capping agent for an addition curable heterocyclic compound for a heat-resistant resin. More particularly, it relates to an end-capping agent having an addition-reactive alicyclic chemical structure. Furthermore, the present invention relates to an easily-moldable polyquinoxaline resin having excellent heat resistance and adhesive strength to reinforcing fibers. More particularly, it relates to a thermosetting quinoxaline resin oligomer which is addition-curable by an alicyclic endo compound present at both ends.

2. Description of the Related Art

With recent rapid progress in space and aircraft industries and electronic instrument, the demand for heat-resistant polymers is rapidly increasing. In this respect, the development of fiber-reinforced composite materials represented by carbon fiber reinforced composites is particularly noticeable.

At the present, a polyimide resin is most widely used as the highly heat-resistant matrix resin for a fiber-reinforced composite. However, since the polyimide resin has an insufficient thermal oxidative stability at high temperatures, or water resistance, the development of a heat-resistant resin free from these problems, which can be used instead of the polyimide resin, is eagerly desired.

A polyquinoxaline resin developed by Hergenrother et al. (J. Polym. Sci. A-1 15, 1453 (1967)) has a superior thermal oxidative stability and water resistance to those of the polyimide resin, and it is therefore expected that this resin will be used as a matrix resin for a high-performance fiber-reinforced composite. However, since a high molecular weight polyquinoxaline resin has a high melt viscosity, it is difficult to impregnate this resin into a reinforcing fiber, and therefore, a high temperature and a high pressure are necessary for the molding. As means for improving the moldability, a method has been examined in which an oligomer having an addition-reactive end group, as is well-known in the field of the polyimide resin.

According to this method, the melt viscosity of the resin is reduced and the flowability of the resin during the cure cycle is improved, and therefore, the molding is facilitated.

For example, there can be mentioned an addition-curable quinoxaline resin oligomer which has an acetylene end group represented by the following formula XII (U.S. Pat. No. 3,975,444), and an addition-curable quinoxaline resin oligomer which has a nitrile end group represented by the following formula XIII (SAMPE, vol. 8, page 114 (1976)). However, the reaction temperature of these oligomers is as high as 350° C. to 400° C., molding is difficult.

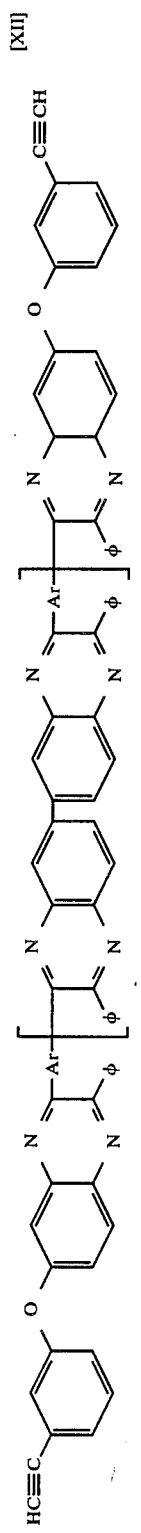
[XII]
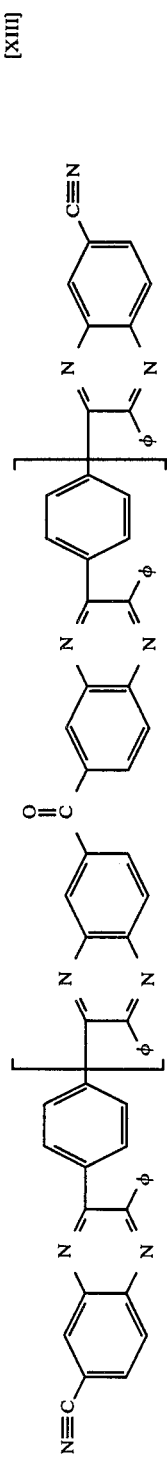
[XIII]

A quinoxaline oligomer represented by the following formula XIV, in which an alicyclic group is introduced (U.S. Pat. No. 3,784,307 and U.S. Pat. No. 3,748,310) has been studied, as for a low temperature addition curable quinoxaline resin.

wherein X represents CO, O, S, $CH_2$, a halogen-substituted methylene group, an alkyl-substituted methylene group having 1 to 6 carbon atoms in the alkyl group or an aryl-substituted methylene group, $Y_1$ through $Y_6$ independently represent a halogen atom, H,

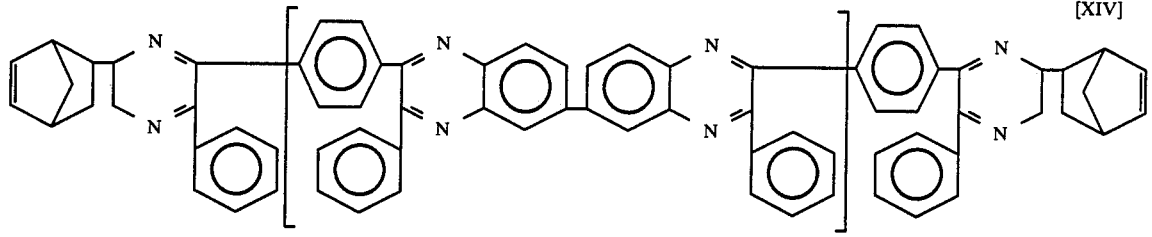

Although these resins have an improved moldability, there are some problems as composite materials in that the mechanical properties such as flexural strength and interlaminar shear strength thereof are poor.

SUMMARY OF THE INVENTION

It is a primary object of the present invention to provide a novel addition curable end-capping agent that can be applied to not only addition-curable quinoxaline compounds but also to other various heat-resistant heterocyclic compounds.

Another object of the present invention is to provide an addition curable thermosetting quinoxaline resin oligomer having an excellent heat resistance and mechanical properties, and an intermediate material for a fiber-reinforced composite.

In accordance with one aspect of the present invention, there is provided an end-capping agent for a heat-resistant heterocyclic compound, which has an alicyclic structure and imide structure represented by the following general formula [I]:

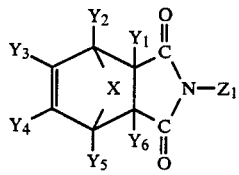

$NO_2$, an aryl group, an alkaryl group preferably having 7 to 12 carbon atoms, an arylalkyl group having 1 to 6 carbon atoms in the alkyl group or an alkyl ether group having 1 to 6 carbon atoms in the alkyl group, and $Z_1$ represents

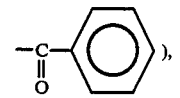

(in which $Q_1$ is $-NH_2$, $-SH$, $-OH$ or

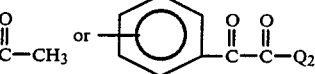

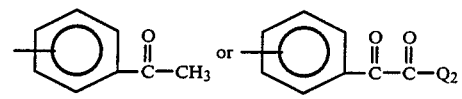

in which $Q_2$ is H, monovalent aliphatic group or a monovalent aromatic group.

In accordance with another aspect of the present invention, there is provided an addition-curable quinoxaline resin oligomer having an alicyclic imide compound at both the terminals of oligomer, which is represented by the following general formula [II] or [III]:

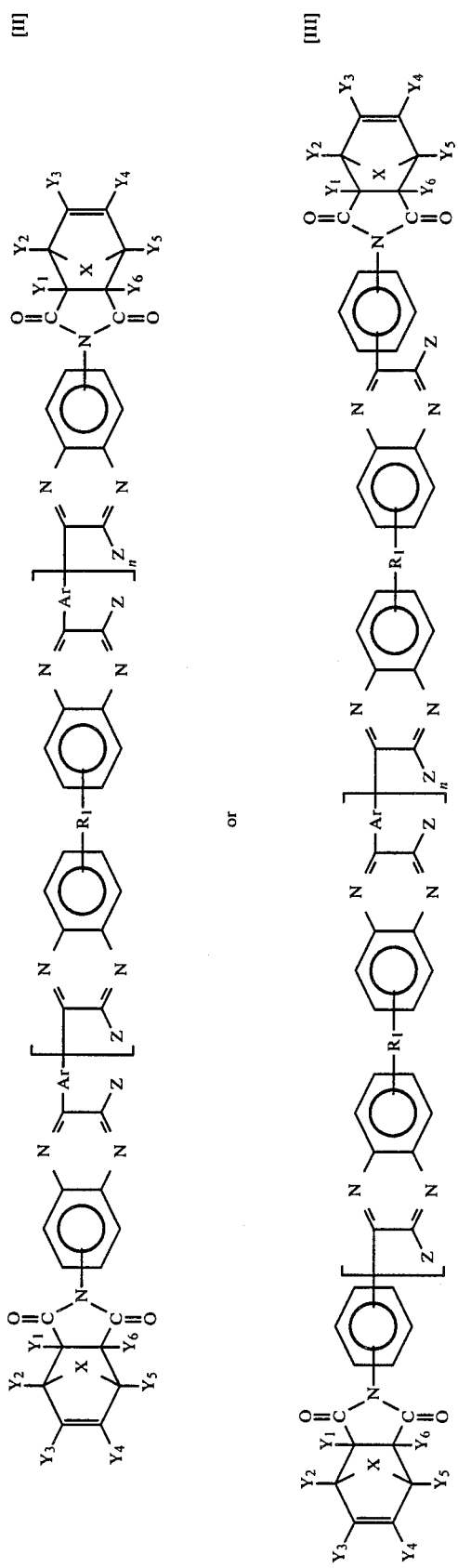

wherein Ar represents

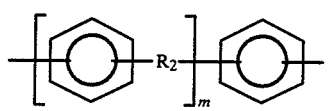

in which m is a number of from 0 to 3, n is a number of from 0 to 10, $R_1$ represents $CH_2$, O, CO, $SO_2$, S or a direct bond, $R_2$ represents $CH_2$, O, CO, $SO_2$, S or a direct bond, X represents $CH_2$ or O, $Y_1$ through $Y_6$ independently represent a halogen atom, H, $NO_2$, an aryl group, an arylalkyl group having 1 to 6 carbon atoms in the alkyl group, an alkaryl group preferably having 7 to 12 carbon atoms, or an alkyl ether group having 1 to 6 carbon atoms in the alkyl group, and Z represents H or

In accordance with still another aspect of the present invention, there is provided an intermediate material for a fiber-reinforced composite, which comprises a reinforcing fiber impregnated with the abovementioned addition-curable quinoxaline resin oligomer or a monomer thereof.

excellent mechanical properties such as the fluxural strength or interlaminar shear strength thereof.

The alicyclic structure referred to in the present invention includes an endo type in which X and N in the general formula I are of the cis-form, and an exo type in which X and N are of the trans-form. Generally, the former type is more stable and has a higher practical utility than the latter. The alicyclic endo structure is characterized in that addition reaction is caused at a temperature lower than 300° C. and therefore, molding is easily accomplished. Especially in the case of an aliphatic structure having O as X, the addition reaction temperature can be advantageously lowered to about 250° C. Furthermore, if an appropriate functional group is selected as Z in the formula I, the end-capping agent can be used for various heat-resistant resins. For example, if aromatic o-diamine and aromatic glyoxalyl are selected, the end-capping agent can be used for quinoxaline resins, and if o-aminobenzophenone and acetylbenzene are selected, the end-capping agent can be used for quinoxaline resins. Moreover, if aromatic o-mercaptoaniline is selected, the end-capping agent can be used for benzothiazole resins, and if aromatic o-hydroxyaniline is selected, the end-capping agent can be used for benzoxazole resins.

(Synthesis of End-capping Agent)

The end-capping agent of the present invention can be synthesized according to the following processes (1) and (2):

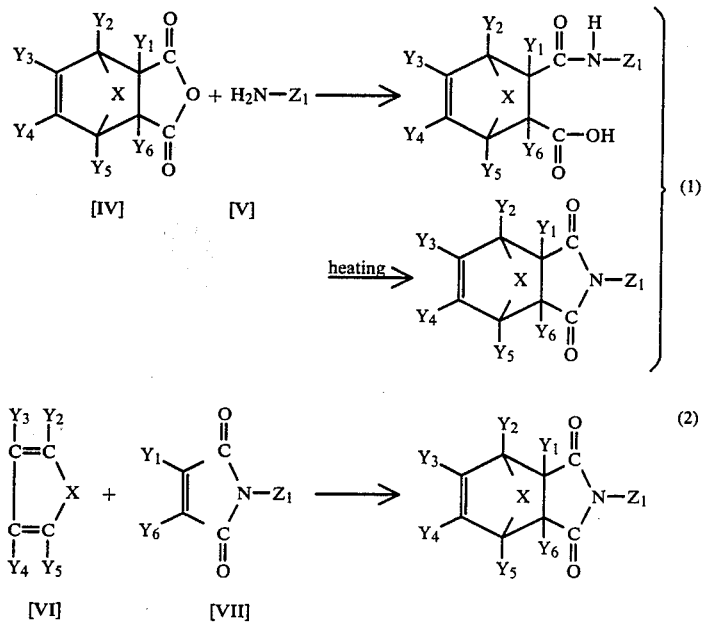

DESCRIPTION OF THE PREFERRED EMBODIMENTS

The end-capping agent of the present invention has an imide structure. An addition-curable quinoxaline oligomer and other various resin oligomers synthesized by using this end-capping agent have a highly improved adhesive strength to reinforcing fibers, especially carbon fibers. Therefore, the composite material made from these Oligomer used as the matrix resin has an In the above formulae, X may be a carbonyl group, an ether group, a sulfide group, a methylene group, a halogen-substituted methylene group, an alkyl-substituted methylene group having 1 to 6 carbon atoms in the alkyl group, and an aryl-substituted methylene group. As $Y_1$ through $Y_6$, there can be mentioned a halogen atom, a hydrogen atom, a nitro group, an aryl group, an arylalkyl group having 1 to 6 carbon atoms in the alkyl group, an alkyl ether group having 1 to 6 carbon atoms in the alkyl group and an alkaryl group preferably having 7 to 12 carbon atoms. The following compounds can be mentioned as the compounds IV and VI.

Compound IV 2,5-Endomethylene-1,2,5,6-tetrahydrophthalic anhydride, 2-methyl-2,5-endomethylene-1,2,5,6-tetrahydrophthalic anhydride, 2-chloro-2,5-endomethylene-1,2,5,6-tetrahydrophtalic anhydride, 2,5-endoxo-1,2,5,6-tetrahydrophthalic anhydride, 2-methyl-2,5-endoxo-1,2,5,6-tetrahydrophthalic anhydride and 2-chloro-5-ethyl-2,5-endoxo-1,2,5,6-tetrahydrophthalic anhydride.

Compound VI

Cyclopentadiene, methylcyclopentadiene, cyclopentadienone, 1,1,2,3,4,5-hexachlorocyclopentadiene, 3,4-diphenylthiophene, furan and 3,4-dimethylfuran.

As the structure of $Z_1$ in the formulae, there can be mentioned

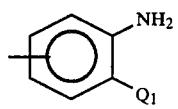

(in which $Q_1$ represents —NH$_2$, —SH,

Compound V 1,2,4-Triaminobenzene, 1,3-diamino-6-mercaptobenzene, 1,4-diamino-2-hydroxybenzene, 2,5-diaminobenzophenone, p-aminoacetophenone and 3-aminobenzyl.

Compound VII 1,2-Diamino-5-maleimidobenzene, 2-mercapto-4-maleimidoaniline, 2-hydroxy-4-dimethylmaleimidoaniline, 2-amino-4-maleimidobenzophenone, p-maleimidoacetophenone and p-maleimidobenzyl.

The amino group in the chemical structure $Z_1$ may be a nitro group according to the synthesis root, and this nitro group may be reduced to an amino group after the reaction (1) or (2). The following compounds may be used as starting materials of the compounds V and VII.

Compound V

2-Nitro-p-phenylenediamine, 3,4-dinitroaniline, 3-mercapto-4-nitroaniline, 3-hydroxy-4-nitroaniline and 2-nitro-5-aminobenzophenone.

Compound VII 1,2-Dinitro-4-maleimidobenzene, 1-nitro-2-mercapto-4-maleimidobenzene, 1-nitro-2-hydroxy-4-diethylmaleimidobenzene and 2-nitro-4-maleimidobenzophenone.

The preparation of an end-capping agent is not particularly limited to the foregoing processes (1) and (2). For example, there may be adopted a process in which 3-nitro-o-phenylenediamine is used as the starting material of the compound V and the end-capping agent is synthesized according to the following reaction (3):

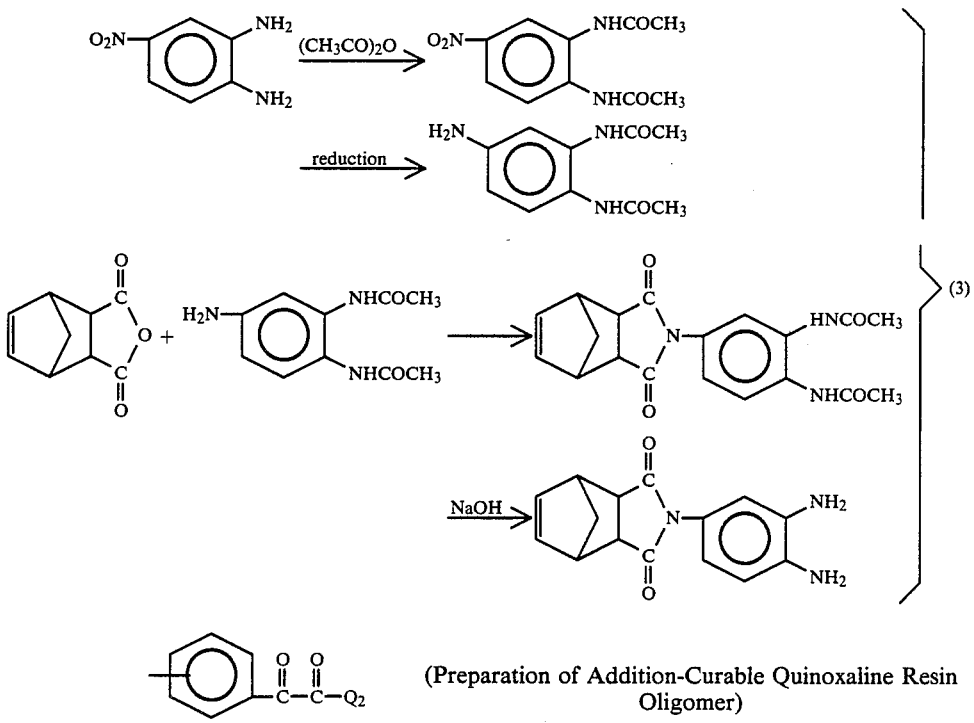

(in which $Q_2$ represents H, a monovalent aliphatic group or a monovalent aromatic group).

The following compounds can be mentioned as the compounds V and VII.

(Preparation of Addition-Curable Quinoxaline Resin Oligomer)

An alicyclic imide compound-containing diamine represented by the following formula VIII or an alicyclic imide compound-containing glyoxalyl compound represented by the formula IX is valuable for an end-cpping agent of the quinoxaline resin oligomer:

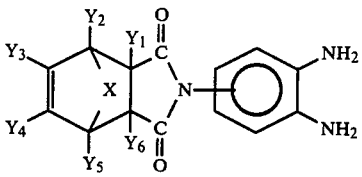 [VIII]

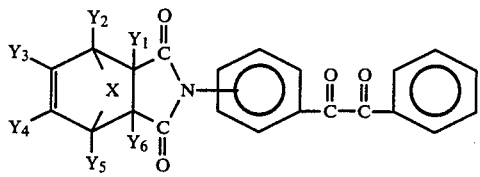 [IX]

wherein X represents CH$_2$ or O, and Y$_1$ through Y$_6$ independently represents a halogen atom, H, NO$_2$, an aryl group, an arylalkyl group having 1 to 6 carbon atoms in the alkyl group, an alkaryl group preferably having 7 to 12 carbon atoms or an alkyl ether group having 1 to 6 carbon atoms in the alkyl group.

When the compound VIII or XI in which X is CH$_2$ is used, a resin curable at about 300° C. is obtained, and when the compound VIII or XI in which X is O is used, a resin curable at a lower temperature, that is, about 250° C., is obtained and the molding temperature can be lowered. The following compounds can be mentioned as the compounds VIII and IX.

Compound VIII 1,2-Diamino-4-(2,5-endomethylene-1,2,5,6-tetrahydro-phthalimido)-benzene, 1,2-diamino-4-(2,5-endoxo-1,2,5,6-tetrahydrophthalimido)benzene and 1,2-diamino-4-(2-methyl-2,5-endoxo-1,2,5,6-tetrahydrophthalimido)benzene.

Compound IX 4-(2,5-Endomethylene-1,2,5,6-tetrahydrophthalimido)benzyl and 4-(2,5-endoxo-1,2,5,6-tetrahydrophthalimido)benzyl.

The polyquinoxaline resin is a polymer obtained by polycondensation of a tetramine with a bisglyoxalyl compound. The addition-polymerizable quinoxaline resin oligomer according to the present invention may be synthesized from a tetramine represented by the following formula X:

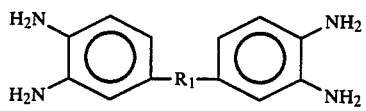 [X]

a bisglyoxalyl compound represented by the following formula XI:

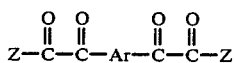 [XI]

and an alicyclic imide compound represented by the above-mentioned formula VIII or IX as the starting monomers. In the above formulae X and XI, Ar represents

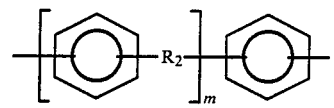

in which m is a number of from 0 to 3, R$_1$ represents CH$_2$, O, CO, SO$_2$, S or a direct bond, R$_2$ represents CH$_2$, O, CO, SO$_2$, S or a direct bond, and Z represents H or

The moldability and heat resistance of the addition-curable quinoxaline resin oligomer according to the present invention depend on the molecular weight of the oligomer represented by the general formula II or III. In order to carry out the present invention, the molecular weight of the oligomer should be adjusted to an optimum value. It is generally preferred that the molecular weight be about 1,000 to about 10,000. Therefore, there is ordinarily adopted a method in which amounts, calculated according to the designated molecular weight, of the alicyclic imide compound (the general formula VIII or IX), the tetramine (the general formula X) and the bisglyoxalyl compound (the general formula XI) are polycondensed in an organic solvent such as m-cresol or dioxane. The obtained prepolymer may be used in the solution state as a varnish for the production of an intermediate material for a fiber-reinforced composite, or the prepolymer is isolated from the solution to obtain a molding powder. Furthermore, an intermediate material for a fiber-reinforced composite can be prepared according to the so-called in-situ polymerization of monomeric reactants using a solution of the calculated amounts of the alicyclic imide compound, tetramine and bisglyoxalyl compound in a polar solvent such as NMP or dioxane.

In the molding intermediate material according to the present invention, it is preferred that the matrix resin content be 25 to 45% by weight. As the reinforcing fiber, there can be used carbon fibers, glass fibers and organic fibers. As the form of the reinforcing fiber, there can be mentioned a fibrous product in which filaments are arranged in one direction, a fibrous product in which filaments are arranged in at least two predetermined directions, a woven fabric, a knitted fabric and the like, and the form of the reinforcing fiber is not particularly critical.

Since the intermediate material for a fiber-reinforced composite according to the present invention can be molded into a large-size structure, the intermediate material is very valuable as an ACM matrix resin for a carbon fiber-reinforced composite widely used in the field of air craft construction or the like.

The present invention will now be described in detail with reference to the following examples.

EXAMPLE 1

This example illustrates the synthesis of 1,2-diamino-4-(2,5-endomethylene-1,2,5,6-tetrahydrophthalimido)-benzene.

(a) 1,2-Dinitro-4-(2,5-endomethylene-1,2,5,6-tetrahydrophthalimido)benzene

In 500 ml of dimethylacetamide was dissolved 198 g or 3,4-dinitroaniline, and a solution of 164 g of 3,6-endomethylene-1,2,3,6-tetrahydrophthalic anhydride in 500 ml of dimethylacetamide was dropped in to the above solution at room temperature with stirring. After completion of the drop wise addition, the mixture was stirred at room temperature for 1 hour, and 150 ml of triethylamine and 150 ml of benzene were added to the mixture, and the reaction was carried out at 140° C. for 3 hours. After the reaction ceased, the reaction mixture was allowed to naturally cool to room temperature and allowed to stand for one whole day and night, whereby a yellow needle crystal was precipitated. The crystal was recovered by filtration and dried in vacuo to obtain 282 g (the yield being 82%) of 1,2-dinitro-4-(2,5-endomethylene-1,2,5,6-tetrahydrophthalimido)benzene. The results of the elementary analysis are as follows.

| Found Values | Calculated Values |
| --- | --- |
| C = 54.60% | C = 54.71% |
| H = 3.39% | H = 3.34% |
| N = 12.93% | N = 12.78% |

(b) 1,2-Diamino-4-(2,5-endomethylene-1,2,5,6-tetrahydrophthalimido)benzene

In 1200 ml of ethyl alcohol was dissolved 200 g of 1,2-dinitro-4-(2,5-endomethylene-1,2,5,6-tetrahydrophthalimido)benzene, 850 g of stannic chloride dihydrate was added to the solution, an reaction was carried out under reflux at boiling point for 4 hours. The reaction solution was cooled to room temperature, poured into water, and neutralized with sodium hydrogencarbonate. Then, the solution was extracted with 3 l of ethyl acetate. Ethyl acetate was removed from the extract by distillation under a reduced pressure to obtain 127 g (a yield of 78%) of a white solid. The results of the elementary analysis are as follows.

| Found Values | Calculated Values |
| --- | --- |
| C = 66.52% | C = 66.91% |
| H = 5.49% | H = 5.57% |
| N = 16.02% | N = 15.61% |

EXAMPLE 2

This example illustrates the synthesis of p-(3,6-endoxo-1,2,3,6-tetrahydrophthalimido)acetophenone.
(a) p-Maleimidoacetophenone In dimethylacetamide, 98 g of maleic anhydride was reacted with 135 g of p-aminoacetophenone at 140° C. for 4 hours. After the reaction, methyl alcohol was added to the reaction solution to precipitate a solid. The precipitate was recovered by filtration and dried in vacuo to obtain 139 g (a yield of 65%) of p-maleimidoacetophenone.
(b) p-(3,6-Endoxo-1,2,3,6-tetrehydrophthalimido)acetophenone To 150 g of benzene were added 34 g of furan and 107 g of p-maleimidoacetophenone, and the mixture was stirred at 80° C. for 15 hours. After the reaction, the reaction mixture was allowed to naturally cool to obtain 103 g (a yield of 73%) of a crystal of p-(3,6-endoxo-1,2,3,6-tetrahydrophthalimido)acetophenone. The results of the elementary analysis are as follows.

| Found Values | Calculated Values |
| --- | --- |
| C = 68.12% | C = 67.84% |
| H = 4.63% | H = 4.59% |
| N = 4.86% | N = 4.94% |

EXAMPLE 3

2-Hydroxy-4-(2,5-endomethylene-1,2,5,6-tetrahydrophthalimido-aniline as the end-capping agent was synthesized in the same manner as described in Example 1, except that 3-hydroxy-4-nitroaniline was used instead of 3,4-dinitroaniline. 300 g of polyphosphoric acid was incorporated with 54.0 g of the end-capping agent, 43.2 g of 3,3'-dihydroxybenzidine, and 49.8 g of terephthalic acid, and the mixture was stirred at 100° C. for 5 hours. After the reaction, the reaction solution was poured into a large quantity of water, and the precipitate was recovered by filtration and dried in vacuo. When the molecular weight of the obtained powder was measured by gel permeation chromatography, it was found that the powder was an oligomer having a number average molecular weight of 1380. The powder was filled in a molding die and press-molded at 290° C. under a pressure of 30 kg/cm$^2$ for 2 hours. The obtained molded body was post-cured in an oven for 6 hours at 316° C. and the glass transition temperature was measured by TMA (Thermo Mechanical Analyzer). It was found that the cured resin had a glass transition temperature of 323° C. and had a good heat resistance. The cured resin was cut by a diamond cutter and the section was observed by a microscope, it was found that there were no voids present and the quality of the cured resin was good.

EXAMPLE 4

This example illustrates the preparation of a quinoxaline resin oligomer.

3,3',4,4'-Tetraminodiphenyl sulfone and p-bis(phenylglyoxalyl)benzene were dissolved at a ratio of 2 moles to 3 moles in dioxane, and reaction was carried out at boiling point for 3 hours. Then, 2 moles of 1,2-diamino-4-(2,5-endomethylene-1,2,5,6-tetrahydrophthalimido)-benzene synthesized in Example 1 were added to the reaction solution and reactioon was carried out at boiling point for 3 hours. Dioxane was removed from the reaction mixture by distillation under a reduced pressure, and the residue was dried in vacuo to completely remove dioxane and obtain a quinoxaline oligomer.

The obtained powder of the quinoxaline resin oligomer was filled in a molding die and press-molded at 290° C. under a pressure of 30 kg/cm$^2$ for 2 hours. The obtained molded resin was post-cured in an oven for 6 hours at 316° C. The glass transition temperature measured by TMA was 366° C. and the cured resin had a good heat resistance.

EXAMPLE 5

This example illustrates the presentation of a fiber-reinforced composite.

A prepreg was prepared according to the drum winding method by using a dioxane solution of the quinoxaline resin oligomer obtained in Example 4 and a carbon fiber (Torayca T400 supplied by Toray) as the reinforcing fiber. The resin content in the obtained prepreg was 32.3% by weight.

The prepreg was cut into pieces having a width of 20 cm and a length of 25 cm, and 10 cut pieces were stacked and molded in an autoclave. More specifically, the temperature was elevated from room temperature to 240° C. at a heating rate of 2.5° C./min and the laminate was maintained at 240° C. for 1 hour. When 15 minutes had passed from the point of the temperature reached 240° C., the pressure in the bag was reduced below 5 mmHg and this reduced pressure was maintained until the completion of the cure cycle. After the temperature had been maintained at 240° C. for 1 hour, the temperature was elevated to 290° C. at a rate of 2.5° C./min, and this elevated temperature of 290° C. was maintained for 2 hours. Then, the temperature was lowered to room temperature. Simultaneously with the initiation of the cure cycle, the pressure in the autoclave was elevated to 14 kg/cm² at a rate of 0.4 kg/cm²/min and this elevated pressure of 14 kg/cm² was maintained until the completion of the cure cycle. After the autoclave molding, the obtained laminate body was post-cured in an oven for 6 hours at 316° C. The composite mechanical properties were measured according to the ASTM method. The flexural strength was 205 kg/mm², the flexural modulus was 13.6 ton/mm², and the interlaminar shear strength was 12.2 kg/mm². The glass transition temperature was 362° C. measured by the TMA method. The retention of flexural strength measured at 250° C. was 84% of that at room temperature, and it was confirmed that the cured laminate had a good heat resistance.

COMPARATIVE EXAMPLE 1

A quinoxaline resin oligomer was synthesized in the same manner as described in Example 4, except that 2,5-endomethylene-1-α,β-diaminoethane-1,2,5,6-tetrahydrobenzene was used instead of 1,2-diamino-4-(2,5-endomethylene-1,2,5,6-tetrahydrophthalimido)benzene, and a carbon fiber composite was molded in the same manner as described in Example 5 by using this quinoxaline resin oligomer.

The glass transition temperature was 354° C. as measured by the TMA method and the heat resistance was good. The flexural strength and the interlaminar shear strength measured according to the ASTM method, were 152 kg/mm² and 8.5 kg/mm² respectively. Thus, it was confirmed that the mechanical properties of the obtained composite were much lower than those of the composite obtained in Example 5.

We claim:

1. An end-capping agent for a heat-resistant heterocyclic compound, which has an alicyclic structure and imide structure represented by the following general formula [I]:

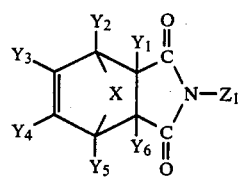

[I]

wherein X represents CO, O, S, CH₂, a halogen substituted methylene group, an alkyl-substituted methylene group having 1 to 6 carbon atoms in the alkyl group or an aryl-substituted methylene group, $Y_1$ through $Y_6$ independently represent a halogen atom, H, $NO_2$, an aryl group, an alkaryl group having 1 to 6 carbon atoms in the alkyl group, an arylalkyl group having 1 to 6 carbon atoms in the alkyl group or an alkyl ether group having 1 to 6 carbon atoms in the alkyl group, and $Z_1$ represents

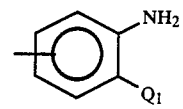

(in which $Q_1$ represents $-NH_2$, $-SH$, $-OH$ or

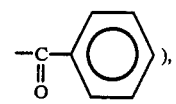

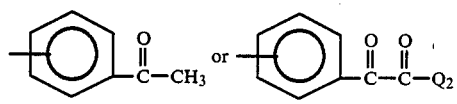

in which $Q_2$ represents H, a monovalent aliphatic group or a monovalent aromatic group.

2. An end-capping agent as set forth in claim 1, which is represented by the following general formula [VIII] or [IX]:

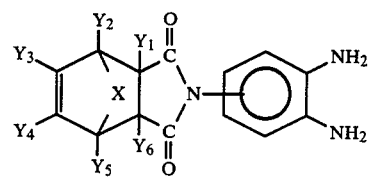

[VIII]

or

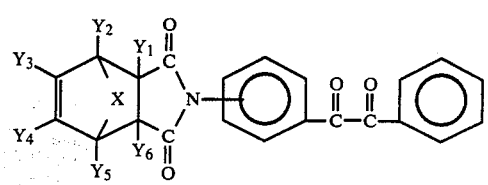

[IX]

wherein X represents CH₂ or O, and $Y_1$ through $Y_6$ independently represents a halogen atom, H, $NO_2$, an aryl group, an arylalkyl group having 1 to 6 carbon atoms in the alkyl group, an alkaryl group having 1 to 6 carbon atoms in the alkyl group or an alkyl ether group having 1 to 6 carbon atoms in the alkyl group.

3. An end-capping agent as set forth in claim 1, which is 1,2-diamino-4-(2,5-endomethylene-1,2,5,6-tetrahydrophthalimido)benzene.

4. An end-capping agent as set forth in claim 1, which is 1,2-diamino-4-(2,5-endoxo-1,2,5,6-tetrahydrophthalimido)benzene.

5. An end-capping agent as set forth in claim 1, which is 1,2-diamino-4-(2-methyl-2,5-endoxo-1,2,5,6-tetrahydrophthalimido)benzene.

6. An end-capping agent as set forth in claim 1, which is 4-(2,5-endomethylene-1,2,5,6-tetrahydrophthalimido)benzyl.

7. An end-capping agent as set forth in claim 1, which is 4-(2,5-endoxo-1,2,5,6-tetrahydrophthalimido)benzyl.

* * * * *